United States Patent [19]

Smith et al.

[11] 4,276,888
[45] Jul. 7, 1981

[54] VITAL FUNCTION MONITOR

[76] Inventors: Charles A. Smith, 46 Hill Rd., Louisville; Thomas J. Hoehler, 2109 Janlyn Rd., Jeffersontown, both of Ky.

[21] Appl. No.: 955,108

[22] Filed: Oct. 26, 1978

[51] Int. Cl.³ .................................. A61N 5/04
[52] U.S. Cl. .......................... 128/706; 128/736; 128/719
[58] Field of Search ............. 128/668, 670-671, 128/696, 700, 708, 716, 719, 736

[56] References Cited

U.S. PATENT DOCUMENTS

| | | | |
|---|---|---|---|
| 3,608,545 | 9/1971 | Novack | 128/700 |
| 3,766,908 | 10/1973 | Haynes | 128/716 |
| 3,841,315 | 10/1974 | Kopp | 128/706 |
| 3,938,507 | 2/1976 | Sarnoff et al. | 128/706 |
| 4,090,504 | 5/1978 | Nathan | 128/736 |

FOREIGN PATENT DOCUMENTS

1224904  3/1971  United Kingdom ............ 128/670

OTHER PUBLICATIONS

Sviridov, A., "Pneumooxyhemograph-3 Instrument for Investigating the Functional State of Blood Circulation and Respiration", Biomed Engr., vol. 7, No. 4, pp. 248-250, Jul.-Aug. 1973, (Pub. May 1974).

*Primary Examiner*—Kyle L. Howell
*Assistant Examiner*—Francis J. Jaworski
*Attorney, Agent, or Firm*—Edward M. Steutermann

[57] ABSTRACT

A multi-function portable patient monitor arrangement having minimal power requirements particularly useful in association with patient transport apparatus to monitor patient functions such as, monitor means to monitor rate of patient heartbeat, body temperature monitor means to detect patient body temperature and patient environment oxygen monitor means to monitor inspired oxygen concentrations in the patient environment, including a direct current voltage at positive source voltage V1 supplied to first voltage reduction means where a positive voltage V2 is supplied at an output from the first voltage reduction means to patient heartbeat monitor means, patient body temperature monitor means, to patient environment oxygen monitor means and to second voltage regulator means where the second voltage regulation means provides output at negative voltage V3 relative to V2 to provide power to the patient body temperature sensor means environmental oxygen monitor means and the heartbeat monitor means.

7 Claims, 7 Drawing Figures

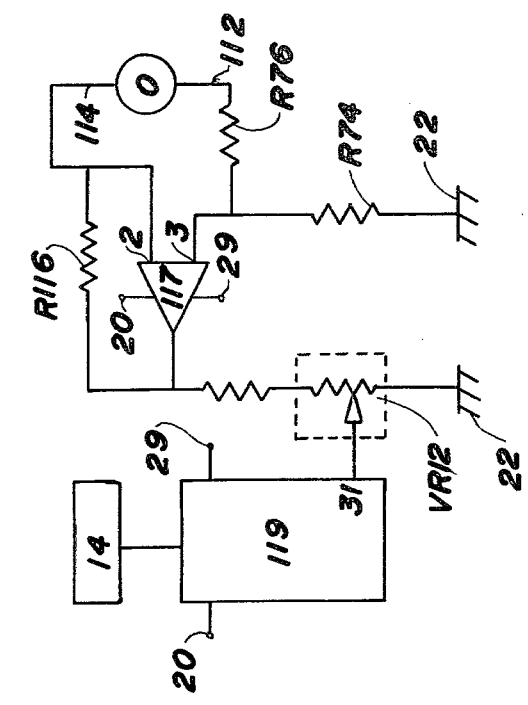
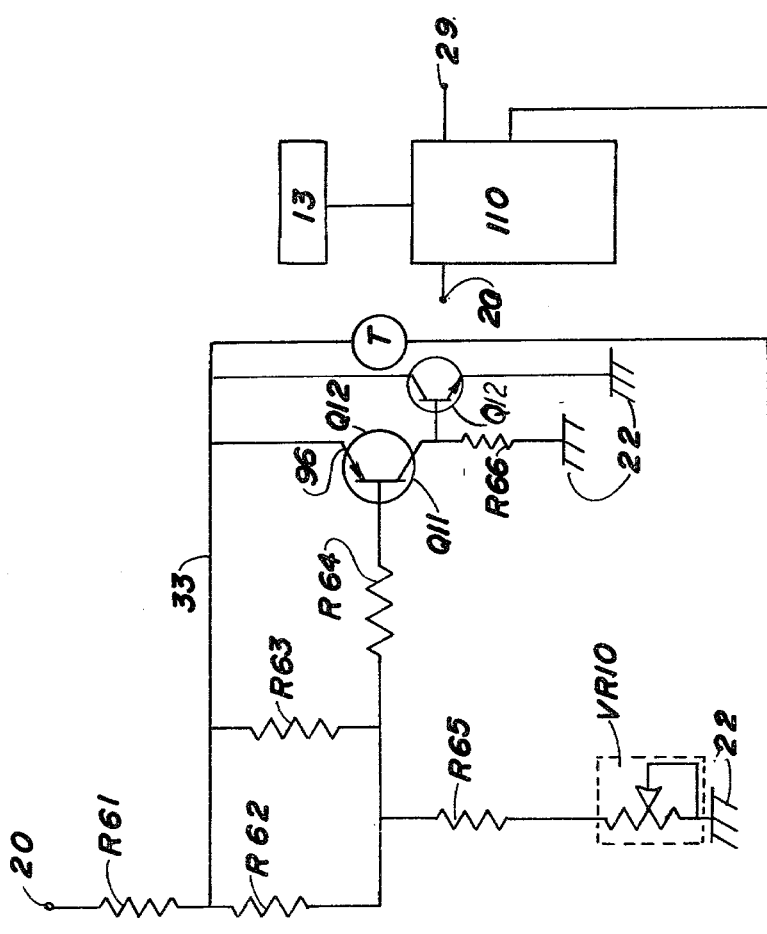
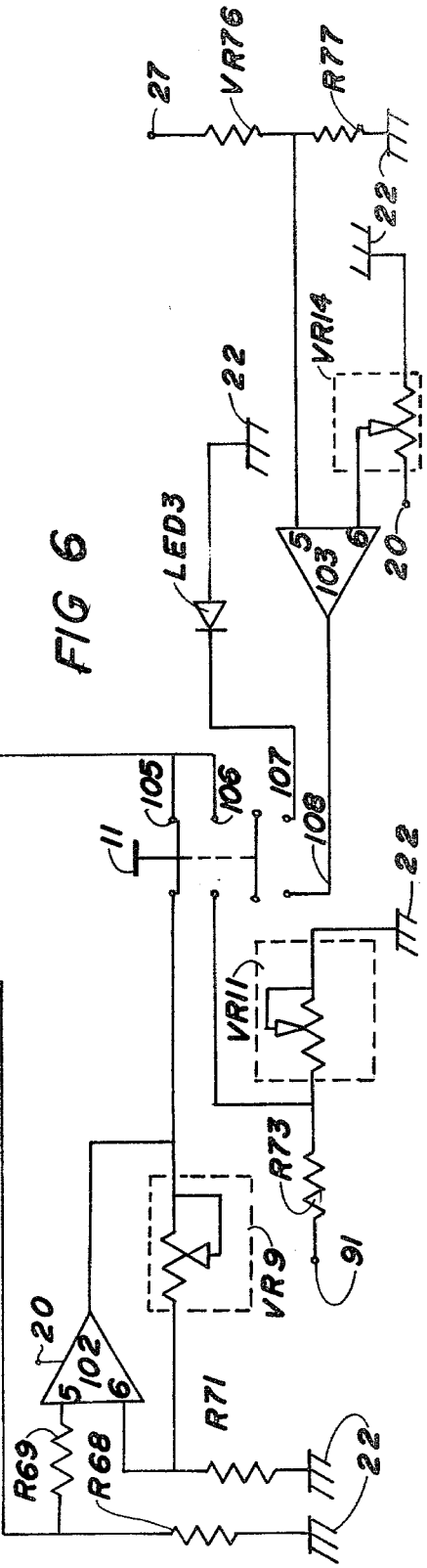
FIG 7
FIG 6

VITAL FUNCTION MONITOR

BACKGROUND OF THE INVENTION

The present invention provides a useful apparatus and means to monitor certain vital signs of a patient under medical care where the device is particularly useful in a transport device, for example, an ambulance transporting the patient (perhaps an infant) to or between hospitals, or in transport devices, for example, in the case of infants, transporting the infant from location to location within a hospital where it is useful to maintain continuous regard to the patient heartbeat rate, body temperature and oxygen concentration inspired by the patient in the transport device or respirator.

In the care of infants requiring assistance, monitors are available in hospitals and nurseries which simultaneously provide many of the monitoring capabilities of devices in accordance with the present invention.

Other devices are available to separately monitor the functions observed by devices in accordance with the present invention but no device is known which accomplishes the combination of the individual monitoring functions with a single, extremely smooth power source.

Prior art devices, where each device monitors a single function, have generally been powered by rechargeable batteries or from AC current, as are known in the art. Because of the power available, and because only a single function is monitored, such prior art devices have not been adapted to minimize power consumption and because of the significant electrical energy required for operation, such prior art devices have not been adaptable for operation with dry cell or other nonrechargeable batteries so that operation is limited to a period of time equal to the effective discharge life of the battery, or recharge facilities must be available.

Moreover, in some instances, several of the single function monitoring devices have been provided in, for example, ambulances, but in ambulances, as in other transport devices, space is at a premium so provision of multiple devices with equal duplication of power supplies unnecessarily consumes space which could be better utilized to store other necessary equipment.

Insofar as known, no portable device is presently available with the combined capability of monitoring heartbeat, body temperature and environmental, and/or inspired oxygen of a patient utilizing a single power source and designed to operate with minimum power requirements so that readily available dry cell batteries can be utilized to furnish the necessary power for a long period of time.

SUMMARY OF THE INVENTION

The present invention provides an economical multifunction patient monitor to efficiently monitor heartbeat rate, body temperature and environmental and/or inspired oxygen concentration of a patient undergoing medical attention which is particularly useful during periods when the patient is being transported where the three parameters can be operated separately or simultaneously.

Morever, devices in accordance with the present invention are compact and portable so that they can be easily transferred from location to location or from one transport device to another with a minimum of effort where the unit can be utilized for all patients, neonates to adults.

Moreover, the devices provided by the present invention are adapted to provide simultaneous or selective digital readout of the functions monitored as well as high-low visual and continuous audible alarms for heartbeat rates outside the preselected range but where the continuous audible alarm can be selectively silenced for a preselected short period of time, for example, two minutes.

Moreover, an audible heartbeat signal can be provided to be transmitted to earphones for use in excessive noise conditions such as ambulances, airplanes or helicopters, and where, in accordance with one feature of the present invention, the heartbeat signal can be heard in the earphones even when the continuous audible alarm is activated.

Moreover, devices in accordance with the present invention can be adapted to permit medical personnel to monitor the condition of the power supply source, for example, a dry cell battery to indicate when a replacement is necessary.

Moreover, devices in accordance with the present invention can be constructed with the circuit elements electrically isolated from the cabinet to prevent damage to the device and/or the patient in the event of exposure of the cabinet to electrical shock.

In accordance with another feature within the scope of the present invention, multiple function monitor devices are provided which are characterized by unusually low power requirements so that the monitors can be operated for long periods of time on the power provided by disposable dry cell electric storage batteries.

Additionally, the present invention provides a temperature monitor circuit which does not require a bridge arrangement as utilized in prior art devices and, further, provided a battery test circuit which provides a direct readout of the voltage of the power supply to the unit to provide means of monitoring the remaining available power to the unit.

More particularly, the present invention provides a portable multifunction patient monitor arrangement particularly useful in monitoring the condition of a patient during transport including a heartbeat frequency monitor means to determine the rate of patient heartbeat, body temperature monitor means to determine patient body temperature, an oxygen monitor means to determine oxygen concentration in the patient environment and direct current source voltage means to provide direct current source voltage at VI to first voltage regulator means adapted to provide direct current power at voltage V2, which is lower than V1 to the heartbeat monitor means and to second voltage regulator means having output voltage V3-1 supplied to the heartbeat monitor means and output voltage V3-2 supplied to the body temperature monitor means and to the oxygen monitor means.

It is to be understood that the drawings and description discussed hereinafter relate to but one example of arrangements within the scope of the present invention and that various modifications thereof within the scope of the present invention will occur to those skilled in the art upon reading the disclosure hereinafter.

BRIEF DESCRIPTION OF THE DRAWINGS

Referring now to the accompanying drawings which illustrate one example of a device within the scope of the present invention:

FIG. 6 is a schematic illustration of an example of a temperature and battery monitor circuit; and FIG. 7 is a schematic illustration of one example of an oxygen monitor circuit.

Figure 1:
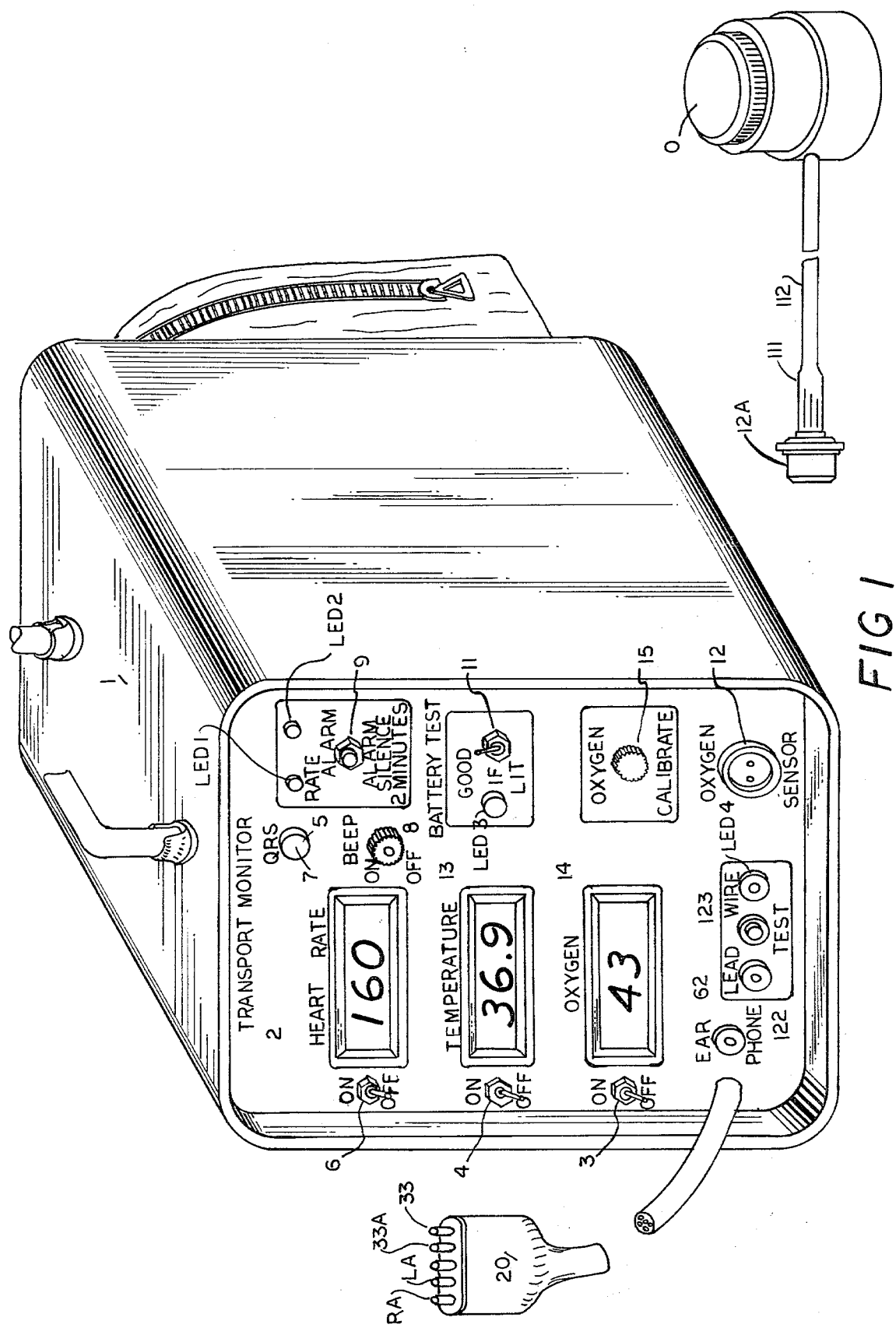
FIG. 1 is a simulation of a casing and operating panel of a device in accordance with the present invention.

Referring first to FIG. 1, the circuitry and elements described hereinafter can be packaged in a case 1 having a front or operating panel 2 to provide the readouts and operating functions as described hereinafter.

Briefly, with respect to the heartbeat monitor described hereinafter, it includes a heartbeat rate readout, which is adapted to utilize light-emitting diodes, as described hereinafter to provide direct reading of display 7 of patient heartbeat in beats per minute. An on-off switch 6 is provided to enable and/or disable the heartbeat rate monitor section. Also, as described in more detail hereinafter, an individual beat indicator 5 can be provided which is actuated by each beat of the patient's heart. Specifically, indicator 5 can be a light-emitting diode activated by the heartbeat rate monitor circuit described hereinafter commonly called a "QRS" indicator because it is activated by the characteristic wave "Q-R-S" pattern of the current generated in normal operation of the heart.

In accordance with another feature of the present invention, audible signals can be generated in response to heartbeat where a volume control and switch combination 8 can be provided to enable and/or disable appropriate circuits described hereinafter to provide an audible "beep" at each heartbeat and also vary the volume of said "beep". Also, for situation when audible beeps cannot be heard or is not desirable, earphone jack 62 can be provided so that the operator or attendant, using an earphone can hear the audible signals signifying each heartbeat.

Additionally, the example in accordance with the present invention is provided with means to provide an alarm (in this case, an audible continuous alarm) where the patient heartbeat rate is in excess of, or below, a preselected frequency range. Because of the importance of heartbeat rate, no means are provided on the outside of the unit to either change the alarm parameters or to disable the alarm except that a preset time delay switch 9 can be provided with associated circuitry (described hereinafter) to silence the continuous alarm for a selected time interval, for example, two minutes. Upon expiration of the time period, the alarm is again actuated if the heartbeat rate remains outside acceptable limits, for example, 75 to 180 beats per minute. In the event the audible alarm is silenced a visual indication is provided during the period the audible alarm is silenced so that the attendant is made aware that a problem continues.

Devices within the scope of the present invention are also adapted to provide direct readout of body temperature, for example, by means of a digital voltmeter as described hereinafter utilizing three-digit light-emitting diodes display 13. A switch 4 can be provided to enable and disable the body temperature function.

Also within the scope of the present invention, a battery test circuit described hereinafter, can be provided to periodically test the capacity of the power supply source, for example, a dry cell arrangement. The battery test circuit can be activated by a normally open spring biased switch 11 and adapted to read out the voltage of the battery at display 13. A visible indication is also provided to indicate battery condition by means of a light-emitting diode 3 on the front panel which comes on if batteries are good.

The final function, that is, the oxygen concentration in the patient atmosphere is enabled by an off-on switch 3 which activates circuitry, described hereinafter, where a lead is provided between a connector 12 and the patient atmosphere. The oxygen concentration in the patient atmosphere is read out by a three-digit light-emitting diode display 14 powered by a digital voltmeter as described hereinafter.

An oxygen analyzer calibration circuit activated by a potentiometer 15 can be provided as described hereinafter to periodically recalibrate the sensor circuit.

As shown, a single lead is provided for the body temperature and heartbeat functions and is permanently connected to the unit to prevent inadvertent separation of the lead from the unit during use.

Figure 2:
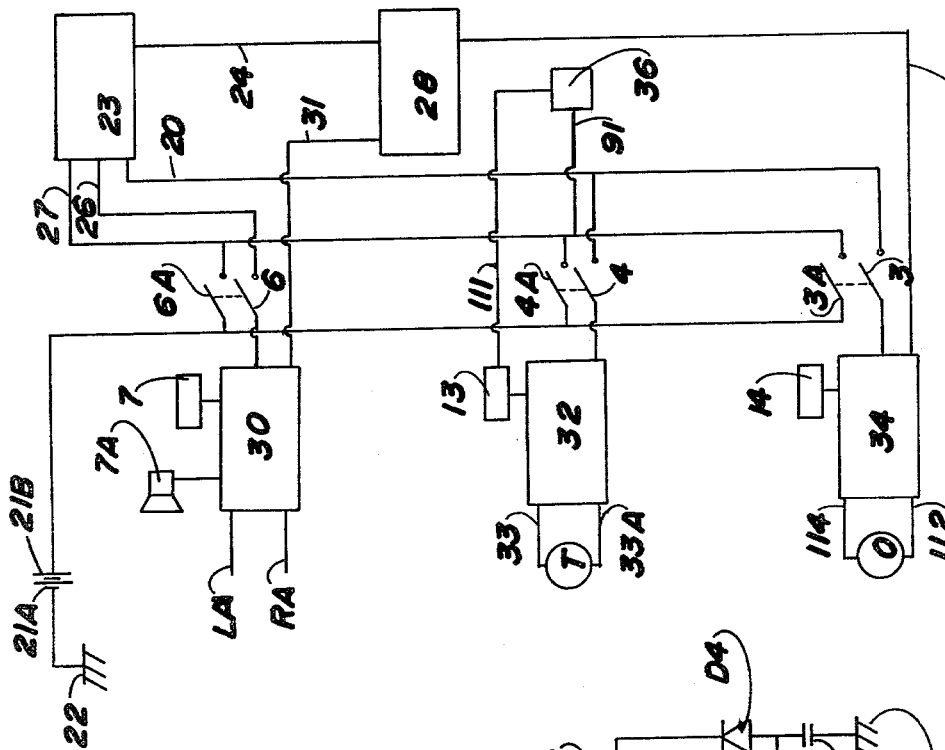
FIG. 2 is a block diagram illustrating the various operational elements of an example of a device within the scope of the present invention.

FIG. 2 is a brief schematic illustration of the arrangement of the functions provided by the present invention with relation to the power supply.

With reference to FIG. 2, a power supply can include two six-volt dry storage batteries 21A and 21B which are provided in series and grounded to an internal floating ground 22 within the unit to provide, for example, +12 volt dc power to a voltage regulator circuit 23 described hereinafter with respect to FIG. 3.

In accordance with one feature of the present invention, three outputs, 20, 24 and 26 are provided from regulator 23. Voltage regulator 23 can be adapted to provide selectively reduced voltage, for example, +5 volts dc at outputs 20, 24 and 26 where a battery test circuit 36 can be provided, for example, between the output from batteries 21A, 21B and output 20 from voltage regulator 23 where the readout from battery test circuit 36 is indicated by display 13, which is shared to read out the body temperature as previously described.

Figure 3:
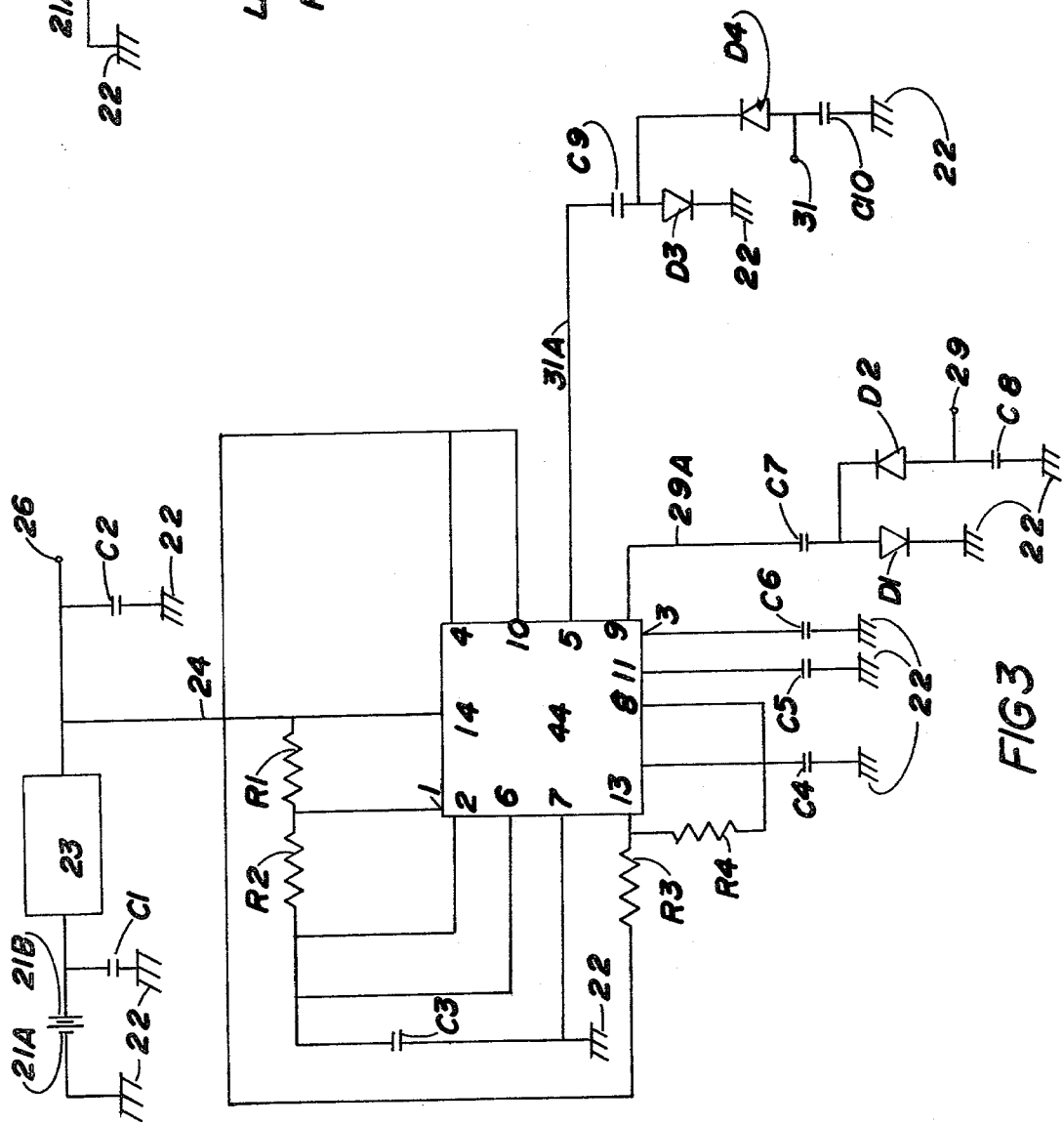
FIG. 3 is a schematic illustration of one example of a power supply circuit within the scope of the present invention.

One output 24 from voltage regulator 23 is provided to a second voltage regulator 28, described more particularly in FIG. 3 where, in accordance with the present invention, two outputs 29 and 31, for example, 2 volts dc, are provided.

Output 20 from voltage regulator 23 is provided to body temperature monitor circuit 32 through a switch 4 when switch 4 is coupled through a co-acting switch 4A in the lead 27 between batteries 21A and 21B and voltage regulator 23. Output 20 is also supplied, through a switch 3 coupled through a co-acting switch 3A in lead 27, to oxygen monitor circuit 34.

The other output 26 from voltage regulator 23 is connected through a switch 6 coupled through a co-acting switch 6A in lead 27 to the heartbeat rate monitor circuit 30. Thus, the heartbeat rate monitor circuit is provided with a power source from regulator 23 separate from the other functions.

Also, it will be noted that in the arrangement shown, because of the arrangement of switches 3, 3A, 4, 4A and 6, 6A, the power circuit is activated when any function is selected by closing any one of the switches 3, 4 or 6.

One output from regulator 28, for example, 31, is supplied to the heartbeat rate monitor circuit 30 described in FIGS. 4 and 5 which, inter alia, provides visual digital indication of heartbeat rate at display 7 and audible signals at horn 7A as described hereinafter. Thus, in accordance with another feature of the present invention, the power supply to the heartbeat monitor circuit is further isolated from the power supply to the other functions to prevent feedback or transient currents from interfering with the heartbeat monitor functions.

An output 29 from regulator 28 is provided to body temperature monitor circuit 32 and oxygen monitor circuit 34.

As previously discussed, one feature of the present invention is a dual supply oscillating DC voltage supply. In the example of FIG. 3, output 24 from regulator 23 (FIG. 2) is connected to an oscillator for example, to the input terminal 44(14) of an MC3556 Motorola (TM) dual timing circuit. Output 24 is connected through resistor R1 to discharge terminal 44(1) of circuit 44 and through resistors R1 and R2 to threshold terminal 44(2) and to trigger terminal 44(6) of circuit 44. Output 24 is also connected through resistors R1 and R2 through capacitor C3 to ground 22 where ground terminal 44(7) of circuit 44 is also connected to ground 22. Output 24 is also connected through resistor R3 to discharge terminal 44(13) of circuit 44 and through resistors R3 and R4 to threshold terminal 44(12) and trigger terminal 44(8) of circuit 44 to ground 22 through capacitor C4. Control terminal 44(3) of circuit 44 is connected to ground 22 through capacitor C5 while control terminal 44(11) is connected to ground 22 through capacitor C6.

Output 29A is connected to output terminal 44(9) and output 31 is connected to output terminal 44(5) of circuit 44. In the arrangement shown, the frequency and value of the output voltage of output 29A at terminal 44(9) is determined by relative values of R1, R2 and C3 while the value and frequency of output 31A is determined by R3, R4 and C4. In the example shown, the values of the respective elements are the same so that the outputs 29A and 31A are equal and of the same frequency and voltage.

Output 29A is connected to ground 22 through a capacitor C7 and diode D1 while output 29 is connected to ground 22 through a capacitor C8 and to output 29A between capacitor C7 and diode D1 through diode D2 so the voltage of output 29 is negative, for example, −2 volts dc, principally.

Likewise, output 31A is connected to ground 22 through capacitor C9 and diode D3 while output 31 is connected through to ground 22 through a capacitor C10 and to output 31A between capacitor C9 and diode D3 through diode D4 so that output 31 also is negative, for example, −2 volts dc.

Figure 4:
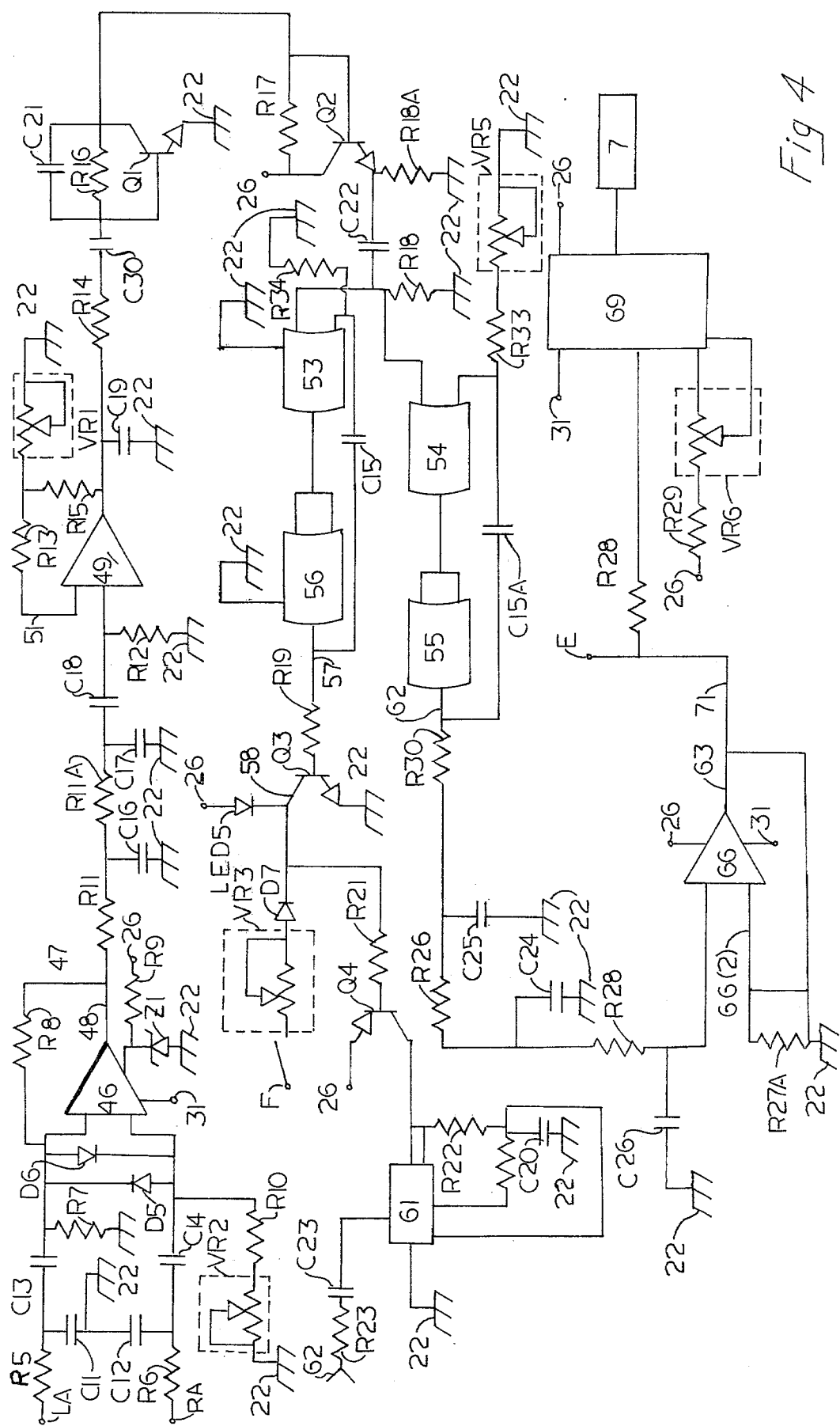
FIG. 4 is a schematic illustration of a portion of an example of a heartbeat rate monitor circuit within the scope of the present invention.

Referring now to FIG. 4 which illustrates, in detail, an example of a heartbeat monitor system in accordance with the present invention, sensors (not shown) are provided to be connected to input terminals, LA and RA, to be connected, respectively, to the left and right sides of a patient to be monitored. It has long been recognized that with every heartbeat in a human body, a current flows in the heart which can be detected by electrodes placed on the left and right sides of the chest. Resistors R5 and R6, for example, 10k ohm resistors. Capacitors C11–C14 and diodes D5 and D6 are provided in association with leads LA and RA as shown to provide defibrillation protection. Lead LA is grounded through resistor R7 to ground 22 while lead RA is grounded through resistor R10 and variable resistor VR2 at 22. Variable resistor VR2 can be provided to null out common mode noise that can be present at RA and LA.

The signal from LA and RA is provided to an amplifier 46, for example, a Raytheon RV 4558 amplifier where a fixed gain feedback loop 47 including a series resistor R8 is provided from a lead, for example LA, to output 48 from amplifier 46. The negative input to amplifier 46 is provided from terminal 31 of regulator 28 (FIG. 2) while the positive input is supplied from terminal 26 of regulator 23 (FIG. 2) through a resistor R9 to the positive input terminal of amplifier 46 and where the positive input terminal is connected to ground 22 through a zener diode Z1.

The output 48 from amplifier 46 is supplied through a filter circuit including series resistors R11A and R11 in series with a capacitor C18 where ground connections 22 are provided between resistors R11 and R11A and resistor R11A and capacitor C18, in each case through a capacitor C16 and C17 respectively. The output 48 is supplied to a similar amplifier 49 where the input is connected to ground 22 through resistor R12 where amplifier 49 is provided with an adjustable gain circuit 51 including resistors R13 and R15 connected to ground 22 through variable resistor VR1 which provides means to adjust the gain.

The output 52 from amplifier 49 is connected to a bypass capacitor C19 to the ground 22 and through resistor R14 and C30 to the base of a transistor Q1 having its emitter connected to ground 22 and its collector connected to its base through resistor R16 and capacitor C21 which are in parallel. The collector of transistor Q1 is also connected to the base of transistor Q2 and through a resistor R17 to supply lead 26 and the collector of transistor Q2 so Q1 triggers Q2 where the output from the emitter of Q2 charges capacitor C22 where each side of capacitor C22 is connected to ground 22 through R18 and R18A respectively and the signal generated is supplied to NOR gates 53, 54. It will be recognized that the signal supplied from Q2 is in the form of pulses reflecting the frequency of the current pulses emanating from the body of the patient and received at terminals LA and RA where the signals are amplified and sharpened by the foregoing described elements. Normally, a heart beats at a rhythm of 60 to 150 beats per minute. The pulses received at NOR gates 53 and 54 are equivalent to the heartbeat rate.

A one-shot multivibrator is formed by NOR gates 53, 56 where the output from gate 56 is connected to the input of gate 53 through C15 and to ground 22 through R34. All gates are supplied with Vcc from input 26 and grounded at 22. The output at 57 reflects the heartbeat rate which is a square wave of every heartbeat and supplied through a resistor R19 to the base of transistor Q3 where the collector terminal 58 is connected through the cathode of a light-emitting diode (LED) 5 which is activated by each QRS wave of each heartbeat to visually signal each heartbeat.

Collector terminal 58 is also connected to the cathode of a diode D7 and a variable resistor VR3 and an off-on switch 8 (see FIG. 1 to terminal F connected with an audible signal, for example, a Sonalert (TM horn 7A FIG. 2) which provides an audible beep in response to every heartbeat when switch 8 is in the closed position where the intensity of the audible signal is set by adjusting resistor VR3.

In certain application, audible signals at the occurence of each heartbeat are desirable and the arrangement shown in FIG. 4 provides an earphone jack 62 (FIG. 1) connected to an audio oscillator 61, for example, an RCA (TM) LM 555, in series with resistor R23 and capacitor C23 where oscillator 61 is supplied with an input signal from a transistor Q4 where the base of transistor Q4 is triggered through a resistor R21 from the collector 58 of transistor Q3 and power supply lead 26 is connected to the emitter 60 of transistor Q4 to power oscillator 61. Thus, an attendant can utilize earphones to listen to the actual heartbeat rate while the alarm is on.

In accordance with another feature of the present invention, a digital heartbeat rate indicator readout circuit can be provided to be activated in response to the output signal 62 of the one-shot multivibrator assembly provided by NOR gates 54, 55. The output (for example, 150 millisecond pulses at a rate proportional to the heartbeat rate) is connected through a resistor R30 to a filter circuit including capacitors C24 and C25 grounded to chassis 22 on opposite sides of a series resistor R26 and through resistors R28 to ground 22 through a capacitor C26 to average the pulses to provide a dc input voltage to an amplifier 66 where the averaged pulse signal is proportional to the heartbeat rate. The output from gate 55 is connected through a series capacitor C15A to the input to gate 54 and through a series resistor R33 and a variable resistor VR5 to ground 22 where the width of the pulses is adjusted by variable resistor VR5 to provide a calibration control for the digital heart rate display.

A gain control circuit for amplifier 66 is provided where an input 66(2) is connected to output 63 through a series resistor R27 and grounded through a resistor R27A to ground 22.

The amplifier 66, for example, an RCA (TM) dual operational amplifier #1458, is supplied from power leads 26 and 31 as shown.

Figure 5:
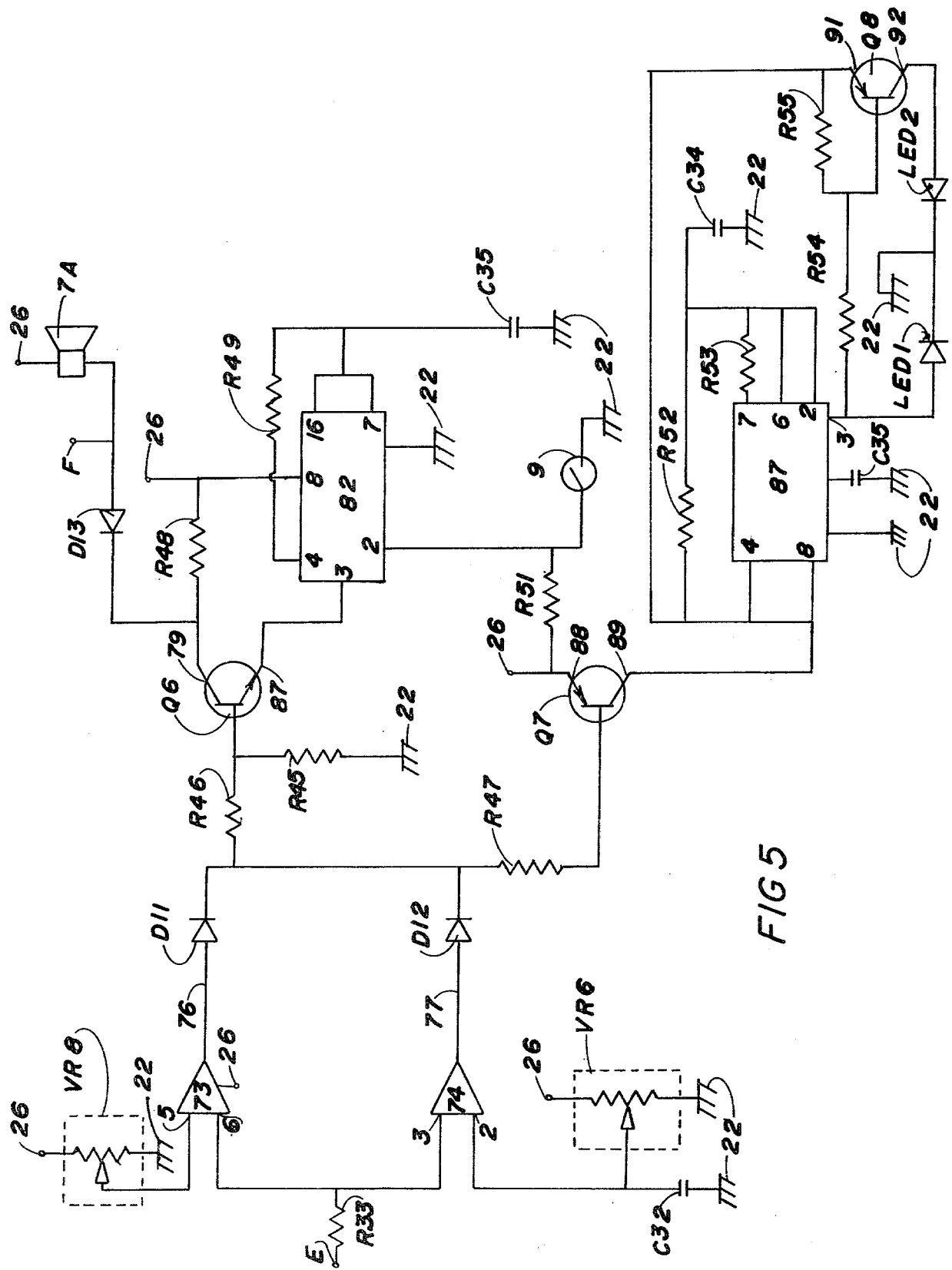
FIG. 5 is a schematic illustration of another portion of an example of a heartbeat rate monitor circuit section.

The output 63 from amplifier 66 is supplied to input terminal E of a high-low alarm circuit described in FIG. 5 and through a resistor R28 to a numerical readout device 69, for example, a 0-2 volt digital voltmeter, for example, a model 1CL7107, manufactured by Intersil, Inc. to provide the three-digit digital read-out display 7 on the face of the unit as shown in FIGS. 1 and 4 where the output reading reflects heartbeats per minute in response to 0-2 vdc changes at the output from amplifier 66.

As previously discussed, devices in accordance with the present invention provide means for an attendant to monitor heartbeat and within the scope of the present invention, alarm means are provided to automatically execute a continuous audible alarm when the heartbeat rate exceeds or falls below a selected rate range.

Referring now to FIG. 5 which is an illustration of one alarm circuit within the scope of the present invention, the circuit is connected, by terminal E to the output of amplifier 66 of FIG. 4 to receive the 0-2 volt input to voltmeter 69 which varies proportionately with a heartbeat rate varying from 0 to 200 beats per minute.

The input from terminal E is connected in series with a resistor R33 to inverting input 73(6) of an operational amplifier 73, for example, a Raytheon (TM) RV 4558 and the noninverting input 74(3) of another operational amplifier 74 of the same type as amplifier 73 to form a dual comparator with high and low limits preset, for example, to be activated by heartbeat rates outside the range of 75 to 170 beats per minute. In the example shown, the noninverting input 73(5) of amplifier 73 which provides the low rate limit, is connected through a capacitor C31 to ground 22 and through a variable resistor VR8 grounded at 22 and connected to power terminal 26 to set the lower limit where the positive voltage is supplied by terminal 26. The output 76 from amplifier 73 is connected through a diode D11 to an output 78 connected to the base of two transistors Q6 and Q7 respectively. Amplifier 74 is situated with terminal E connected to one noninverting input 74(3) and with one inverting input 74(2) connected to ground 22 through a capacitor C32 and to the output of a variable resistor VR6 connected at one end to ground 22 and at the other end to terminal 26 where variable resistor VR6 is used to set the high limit for heartbeat rate. The output 77 from amplifier 74 is connected to a diode D12 and tied to output 78.

In the configuration shown, positive outputs 76 and 77 of amplifiers 73 and 74 are "or'd" together by diodes D11 and D12 and connected to the base of transistor Q6 so when either the high or low level heartbeat rate is exceeded, the output at 78 from amplifiers 73 and 74 goes from 0 to, for example +5 volts to "turn on" transistor Q6 having its collector 79 connected through the cathode of a diode D13 to horn 7A to close a circuit through horn 7A for example, a Sonalert (TM) horn, from terminal 26. In this mode, that is with the horn operating to announce that the limits of heartbeat rate have been exceeded, the attendant can still hear the heartbeat rate by earphones connected through jack 62 (FIG. 4).

In accordance with one feature of the example of the present invention shown in FIG. 5, means can be provided to silence horn 7A for a selected period of time but not to turn the horn off. In the example shown in FIG. 5, terminal 26 is connected to the reset 82(4) and collector supply terminal 82(8) of an integrated circuit time delay or oscillator device 82, for example, an RCA (TM) Model NE555 timer. The output 82(3) from timer 82 is connected to the emitter of transistor Q6 where output 82(3) is normally 0 vdc so that the circuit through terminal 26, horn 7A and transistor Q6 can be completed. Reset terminal 82(4) and collector supply terminal 82(8) are connected in series with a resistor R49 and capacitor C33 to ground 22 where the threshold terminal 82(6) and discharge terminal 82(7) are connected to ground 22 through capacitor C33.

In accordance with the application shown, trigger terminal 82(2) of oscillator 82 can be connected through switch 9 (see FIG. 1) to ground 22 so when terminal 82(2) which is normally kept at 30 5 v is grounded by closing normally open terminal switch 9, terminal 82(3) goes to, for example, +5 vdc and turns off transistor Q6. The period of timer 82 is preset for a selected value, for example, two minutes, so horn 7A is silenced for the time period.

Also, within the scope of the present invention, a visible signal can be provided, other than readout 7, to indicate that either the preset high or low limit has been exceeded. In this regard, output 78 from diodes D11 and D12 is connected through a resistor R47 to the base of a transistor Q7 where the emitter 88 is connected to supply term 26 while the collector 89 of transistor Q7 is connected to the collector supply terminal 87(8) and reset terminal terminal 87(4) of a second timer 87, for example, an RCA (TM) Model NE555 timer. Collector 89 of transistor Q7 is also connected through a resistor R52 and capacitor C34 to ground 22 and through resistors R52 and R53 to discharge terminal 87(7) of timer 87 and through resistor R52 to threshold terminal 87(6) and trigger terminal 87(2) of timer 87. Output terminal 87(3) of timer 87 is also connected to the anode of a light-emitting diode (LED) 1 (see FIG. 1).

To provide the "wig-wag" signal, the collector 89 of transistor Q7 is also connected to the emitter 91 of a transistor Q8 where the base of transistor Q8 is connected through a resistor R54 to output terminal 87(3) of timer 87 and is shunted to the emitter terminal of transistor Q8 through a resistor R55.

Collector 92 of transistor Q8 is connected to the anode of a light-emitting diode LED2 (see FIG. 1) where the cathodes of LED1 and LED2 are tied together and to ground 22, as shown.

In the arrangement shown, LED1 and LED2 are alternately lit when transistor Q7 is gated by output 78 from diodes D11 and D12 where the collector terminal 92 of transistor Q8 and the output 87(3) alternately flash LED2 and LED1 respectively and the period of the cycle is determined by the preselected characteristics of timer 87.

When the heartbeat rate returns to the selected rate, the output 78 from amplifier 73 and 74 goes to 0 so transistors Q6 and Q7 go to the new conduction state and horn 7A is silenced and diodes LED1 and LED2 are turned off.

TEMPERATURE FUNCTION

As previously discussed, devices in accordance with the present invention include means to monitor patient temperature.

The patient temperature sensing circuit 32 (FIG. 1), described hereinafter with respect to FIG. 6, is connected to terminal 29 from voltage regulator 28 and to terminal 20 from first stage voltage regulator 23.

As previously described, switch 4A (FIG. 1) is provided in the lead 27 from the output of batteries 21A, 21B to voltage regulator 23 and co-acting switch 4 (FIG. 1) is provided to close a circuit from voltage regulator 23 to temperature sensing circuit 32.

As shown in FIG. 2, a battery test circuit 36, described in FIG. 6 is provided to be connected by lead 91 to output 27 from batteries 21A and 21B to provide an instantaneous check of the remaining life in the batteries as reflected at display 13 of temperature monitor circuit 32 as described hereinafter.

In this regard, a third co-acting contact 106 operated by pushbutton 11 on the operating panel (FIG. 1) can be provided in output lead 93 from battery test circuit 36 to display 13 normally utilized to read out patient temperature and a cooperative contact 105 in the readout circuit from temperature circuit 30 to display 13 are disabled when contacts 106 is closed so that display 13 reflects output voltage of batteries 21A, 21B.

Referring now to FIG. 6, one temperature measuring circuit 32 in accordance with the present invention is shown including an adjustable voltage regulator supplied from terminal 20 of voltage regulator 23 through a resistor R61 to lead 33. As shown, a temperature compensating resistor R62 and a base resistor R63 are provided in parallel from lead 33 where the ends of resistors R62 and R63 are tied together to resistor R65 and variable resistor VR10 (as shown) and through a resistor R64 to the base of a transistor Q11 where emitter 96 of transistor Q11 is connected to lead 33 and the collector 97 is connected to the base of a second transistor Q12 and through a resistor R66 to ground 22. The collector of transistor Q12 is connected to lead 33 and the emitter to ground 22.

In accordance with one feature of the present invention, the base of transistor Q11 is connected to ground 22 through resistors R64 and R65 and variable resistor VR10 so that VR10 can be utilized to provide a selected excitation voltage, for example, 1.12 volts in lead 33.

A thermistor T can be provided which, as is known in the art, can be applied to a selected part of the patient to monitor temperature, for example, the skin of the patient, and connected at one side to lead 33 where the other end is connected to return lead 33A as described hereinafter.

In accordance with another feature of the present invention, return lead 33A can be connected to ground 22 through a resistor R68 and through a resistor R69 to a noninverting input 102(5) of an amplifier device 102, for example, an RCA (TM) Model RV 4558 operational amplifier. A gain control circuit connected from an inverting input terminal 102 (6) to ground 22 through resistor R71 and to output 98 of amplifier 102 by means of variable resistor VR9 can be provided. Output 98 is supplied through normally closed contacts 105 of switch 11 to a digital voltmeter 102, for example, an Intersil Inc. (TM) Model 1CL7107 having a light-emitting diode display 13 to provide direct readout of patient temperature where the output of amplifier 102 is typically adapted to provide an output voltage of 100 to 500 millivolts corresponding to a temperature of 10 to 50 degrees centigrade in response to an excitation voltage of 1.12 voltage at lead 33 so the patient temperature is read out directly at display 13. It will be noted that the arrangement in accordance with the foregoing provides a means for temperature measurement without the use of a bridge circuit common in other arrangements where the bridge is used to balance voltage to determine temperature.

Also, as previously discussed, display 13 can be utilized to indicate the condition of batteries 21A, 21B. In this regard, two means of battery condition indication can be provided together or alternately.

Specifically, as shown in FIG. 6, the input to a direct voltage readout circuit 36 is provided from output 27 of the batteries 21A, 21B (FIG. 2). Lead 91 is connected to ground through R73 and VR11. Lead 111 connected at the junction of R73 and VR11 applies a reduced voltage preselected by adjustment of VR11 to the input of DVM 102 when pushbutton 11 is pressed for direct reading of the battery voltage at display 13.

Additionally, contacts 107 of a "go-no go" battery indicator can be provided to be closed when contacts 106 are closed. The circuit, described hereinafter to indicate acceptable battery conditions, can be adapted to activate a light-emitting diode LED 3 (FIG. 1) when the battery is in acceptable condition.

Specifically, lead 91 from battery output 27 (FIG. 2) is connected to ground 22 through two series resistors R76, R77 where a noninverting input 103(5) to a dual-operational amplifier for example, an RCA (TM) Model 4558, is connected between resistors R76 and R77 while the associated inverting input is connected to one terminal of a variable resistor VR14 to ground 22 having its associated terminal where the other terminal of variable resistor VR14 is connected to terminal 20. The output 108 from amplifier 103 is connected through contacts 107 to the anode of light-emitting diode 12 where the cathode is connected to ground 22. The arrangement described supra provides a comparator circuit to sense whether the battery voltage at output 27 is above a preset minimum determined by the setting of variable resistor VR14, for example 7 volts dc. When the voltage exceeds the preset minimum, the output of amplifier 103, the output of the comparitor is high and will light light-emitting diode 12 to indicate the batteries are good.

OXYGEN MONITOR FUNCTION

As previously discussed, devices in accordance with the present invention are further adapted to selectively monitor oxygen concentration of the air inspired by patients. The oxygen concentration can be monitored in the atmosphere in a patient encosure or, when the patient is supplied with air from a respiratory assistance system, the oxygen concentration is monitored in the oxygen supply system.

Referring to FIG. 7, one output 114 from the oxygen sensor O, for example, as provided by Bio Marine Industries, Inc. (TM) which provides a linear voltage output in response to oxygen concentration is supplied to an inverting input 117 (2) of dual-operational amplifier 117, for example, an RCA (TM) Model RV 4558 while lead 112 from sensor O is supplied to a noninverting input 117 (3) of amplifier through an appropriate resistor R76. Input 117 (3) is connected to ground 22 through a resistor R74. Terminal 117 (4) is connected to lead 29 to supply −2 vdc to amplifier 117. Input 117 (2) is connected to output 115 through resistor R116 to provide a gain control loop. The output 115 is connected to ground 22 through R77 and VR12. An adjustable voltage at the sliding (wiper) 119 (31) contact of VR12 is applied to input 119 (31) of a digital voltmeter, for example, an Intersil (TM) Model 7107 where the elements previously described are selected so oxygen concentration reads out on a display 14 and can be calibrated by variable resistor VR12.

LEAD TEST

In device of the type described herein the wire leads utilized for input to this unit are regularly flexed and break so that, particularly the insulation on the leads is colored, it is difficult to determine whether a lead is broken. Accordingly, a lead test arrangement 121 is provided (see FIG. 1) where a jack 122 is provided connected to a source of voltage for example terminal 26 and a snap connector 123 is provided connected to ground where an indicator LED 4 is provided in series with connector 123 so a lead wire can be tested by connecting the lead between terminals 122 and 123 so a indicator LED 4 lights if the lead wire is good.

The foregoing is but one example of an arrangement in accordance with the present invention and it will be recognized that various other arrangements within the scope of the present invention will become obvious to those skilled in the art upon reading the foregoing disclosure.

The invention claimed is:

1. A multi-function patient monitor arrangment including patient heartbeat rate monitor means, patient body temperature monitor means, and patient oxygen concentration sensor means, power supply means to supply direct current voltage at positive source voltage V1, first voltage regulator means connected to the output of power supply and having first and second and third output means to supply positive dc voltage V2 where the voltage V2 is less than V1, second voltage regulator having an input connected to an said third output from said first voltage regulator and having first and second voltage regulator output means to supply a voltage V3 which is negative, relative to voltages V1 and V2 wherein said first output of said first voltage regulator means is supplied only to said heartbeat rate monitor means and second output means is supplied to said patient body temperature monitor means and said patient oxygen concentration sensor means and said first output of the second voltage regulator means is selectively supplied to said patient heartbeat rate monitor means and said second second voltage regulator means output is supplied to said patient temperature monitor means and said patient oxygen concentration monitor means.

2. The invention of claim 1 wherein the heartbeat rate monitor means includes sensor means to detect electric current flowing within the patient's body at the occurence of each heartbeat, signal generator means to generate and transmit a heart beat signal at each heartbeat amplifier means to receive said heartbeat signal and amplify each said heartbeat signal where said amplifier means has output means to transmit said amplified heartbeat signal, gate means to receive each amplified heartbeat signal whereby the period of each pulse is equalized and where said gate means provides an output signal including pulse signals of generally equal period and amplitude, integrator means having an input to receive said pulse signals from said gate means to provide an output signal of variable voltage determined by the rate of transmission of said pulsed signals, indicator means directly responsive to the output voltage from said integrator means as a numerical character proportional to the rate of patient heartbeat.

3. The invention of claim 2 wherein the output from said integrator means is supplied to heartbeat alarm means responsive to a selected low voltage supply from said regulator means and to a selected high voltage supply from said regulator means whereby said alarm means is actuated when the patient's heartbeat falls below a preselected minimum and exceeds a preselected maximum.

4. The invention of claim 2 including sound generator means connected to the output of said gate means whereby an audible signal is generated at each pulse supplied from said gate means.

5. The invention of claim 2 including light-emitting alarm means and comparitor means to actuate said light-emitting alarm means having an input connected to said gate output to be actuated in response to heartbeat rate in excess of or below a preselected heartbeat range to indicate out-of-range patient heartbeat rate.

6. The invention of claim 1 wherein said temperature monitor means includes temperature sensing means having an electrical resistance proportional to a temperature of said sensor means, with sensor power supply means including third voltage regulator means connected to the output of said first voltage regulator means having an output, at a selected voltage V4, connected to the input of said temperature sensor means where the output of said temperature sensor means is connected to signal amplifier means whereby the current flowing through said temperature sensor means is proportional to the temperature sensed by said sensor means and where output of said amplifier means is supplied to digital readout means indicating the temperature of said sensor.

7. The invention of claim 1 including lead wire means from heartbeat sensor means and lead wire means from temperature sensor means wherein said lead wire means from said heartbeat sensor means and said lead wire means from said temperature sensor are combined along a portion of the length of each within a single sheath means.

* * * * *